(12) United States Patent
Suzuki (10) Patent No.: US 8,113,656 B2
(45) Date of Patent: Feb. 14, 2012

(54) OPHTHALMIC PHOTOGRAPHY APPARATUS

(75) Inventor: Takayoshi Suzuki, Hamamatsu (JP)

(73) Assignee: Kowa Company Ltd. (JP)

( * ) Notice: Subject to any disclaimer, the term of this patent is extended or adjusted under 35 U.S.C. 154(b) by 21 days.

(21) Appl. No.: 12/804,131

(22) Filed: Jul. 14, 2010

(65) Prior Publication Data

US 2010/0283971 A1    Nov. 11, 2010

Related U.S. Application Data

(62) Division of application No. 12/215,170, filed on Jun. 25, 2008, now abandoned.

(30) Foreign Application Priority Data

Jan. 16, 2008  (JP) ..................................... 2008-6399

(51) Int. Cl.
*A61B 3/14*   (2006.01)
*A61B 3/10*   (2006.01)

(52) U.S. Cl. .......................... 351/207; 351/206; 351/216

(58) Field of Classification Search ................... 351/206, 351/207, 208, 216
See application file for complete search history.

(56) References Cited

U.S. PATENT DOCUMENTS

| 5,713,047 A * | 1/1998 | Kohayakawa ................ 351/206 |
| 2007/0132951 A1 * | 6/2007 | Suzuki .......................... 351/206 |

* cited by examiner

*Primary Examiner* — Ricky Mack
*Assistant Examiner* — Zachary Wilkes
(74) *Attorney, Agent, or Firm* — Adams & Wilks (57) ABSTRACT

A monocular image of a fundus of an eye under examination is captured via a photographic stop for monocular photography, and two stereographically viewed images are captured with a parallax via two photographic stops for stereographic photography that are decentered from a photographic optical axis. Defocused images are captured in the stereographic photography due to the deviation of the photographic stops from the optical axis. A corrective lens is inserted into the photographic optical path in order to correct the defocus in the stereographic photography. This makes it possible to readily correct defocus generated by deviation of the photographic stops from the photographic optical axis even when switching between monocular and stereographic photography modes.

10 Claims, 9 Drawing Sheets

OPHTHALMIC PHOTOGRAPHY APPARATUS

CROSS REFERENCE TO RELATED APPLICATION

The present application is a division of U.S. application Ser. No. 12/215,170, filed Jun. 25, 2008, now abandoned which is hereby incorporated by reference, and priority thereto for common subject matter is hereby claimed.

BACKGROUND OF THE INVENTION

1. Field of the Invention

The present invention relates to an ophthalmic photography apparatus, and more particularly an ophthalmic photography apparatus that is capable of capturing a monocular image of an ocular fundus and stereographically viewed images thereof.

2. Description of the Prior Art

Fundus cameras are conventionally known wherein a photographic stop having two left and right apertures (two-aperture stop) is disposed in a position conjugate with an anterior ocular segment (conjugate with a pupil) of an eye under examination. Reflected light from an ocular fundus passing through the apertures is captured as stereographically viewed left and right images by a film or an imaging element.

Fundus cameras are also known wherein a stereographic photography function is incorporated into a typical fundus camera having an illumination stop and a photographic stop, which are interlinked so as to be able of capturing monocular images and stereographically viewed images (Japanese Laid-open Patent Publication No. 2007-185324).

Fundus cameras are also known in which the wavelength of illuminating light is selected to correct a misalignment of focusing position because the ocular fundus is brought out of focus during specialized photography such as fluorescence photography (Japanese Laid-open Patent Publication No. 2000-268733).

A fundus camera capable of monocular photography and stereographic photography as described in the abovementioned Japanese Laid-open Patent Publication No. 2007-185324 can capture a clear fundus image when the ocular fundus is brought into focus using the photographic stop for monocular photography. However, when the two-aperture stop is selected in this state for stereographic photography, drawbacks are manifested in that defocus occurs and a clear fundus image cannot be obtained. The problems arise from a change in the optical length due to the fact that the position of the apertures used for stereographic photography deviate from the photographic optical axis.

It is therefore an object of the present invention to provide an ophthalmic photography apparatus capable of readily correcting defocus generated by deviation of the apertures of a photographic stop from the photographic optical axis even when switching between monocular photography and stereographic photography.

SUMMARY OF THE INVENTION

An ophthalmic photography apparatus according to the present invention comprises imaging means for capturing a monocular image of a fundus of an eye under examination via a photographic stop for monocular photography and capturing stereographically viewed images of the fundus with a parallax via two photographic stops for stereographic photography that are decentered relative to a photographic optical axis; and a corrective optical element for correcting defocus resulting from the photographic stops for stereographic photography that are decentered relative to the photographic optical axis.

According to the present invention, an ophthalmic photography apparatus comprises imaging means for capturing a monocular image of a fundus of an eye under examination via a photographic stop for monocular photography and capturing stereographically viewed images of the fundus with a parallax via two photographic stops for stereographic photography that are decentered relative to a photographic optical axis; and an optical element capable of moving along the photographic optical axis to bring the fundus into focus; wherein in monocular or stereographic photography the optical element or imaging means is caused for focus adjustment to move along the photographic optical axis by a length corresponding to a difference between a length of an optical path in the monocular photography and a length of an optical path in the stereographic photography.

Furthermore, an ophthalmic photography apparatus according to the present invention comprises an illuminating optical system for illuminating a fundus of an eye under examination via an objective lens; a black spot plate disposed in the illuminating optical system for withdrawing needless light that has been reflected by a surface of the objective lens; a photographic optical system for guiding light from the fundus through the objective lens to imaging means via a photographic stop; and means for selecting the photographic stop in different positions; wherein a black spot that is formed on the black spot plate is changed in position, shape, size and quantity depending upon the selected photographic stop.

In the present invention, defocus generated by deviation of the photographic stops from the photographic optical axis can be readily corrected even when switching between monocular and stereographic photography modes, thereby allowing the clear fundus images to be obtained in both the monocular and stereographic photography modes.

Further features of the invention, its nature and various advantages will be more apparent from the accompanying drawings and following detailed description of the invention.

DESCRIPTION OF THE PREFERRED EMBODIMENTS

The present invention will now be described in detail with reference to the embodiments shown in the attached drawings.

Figure 1:
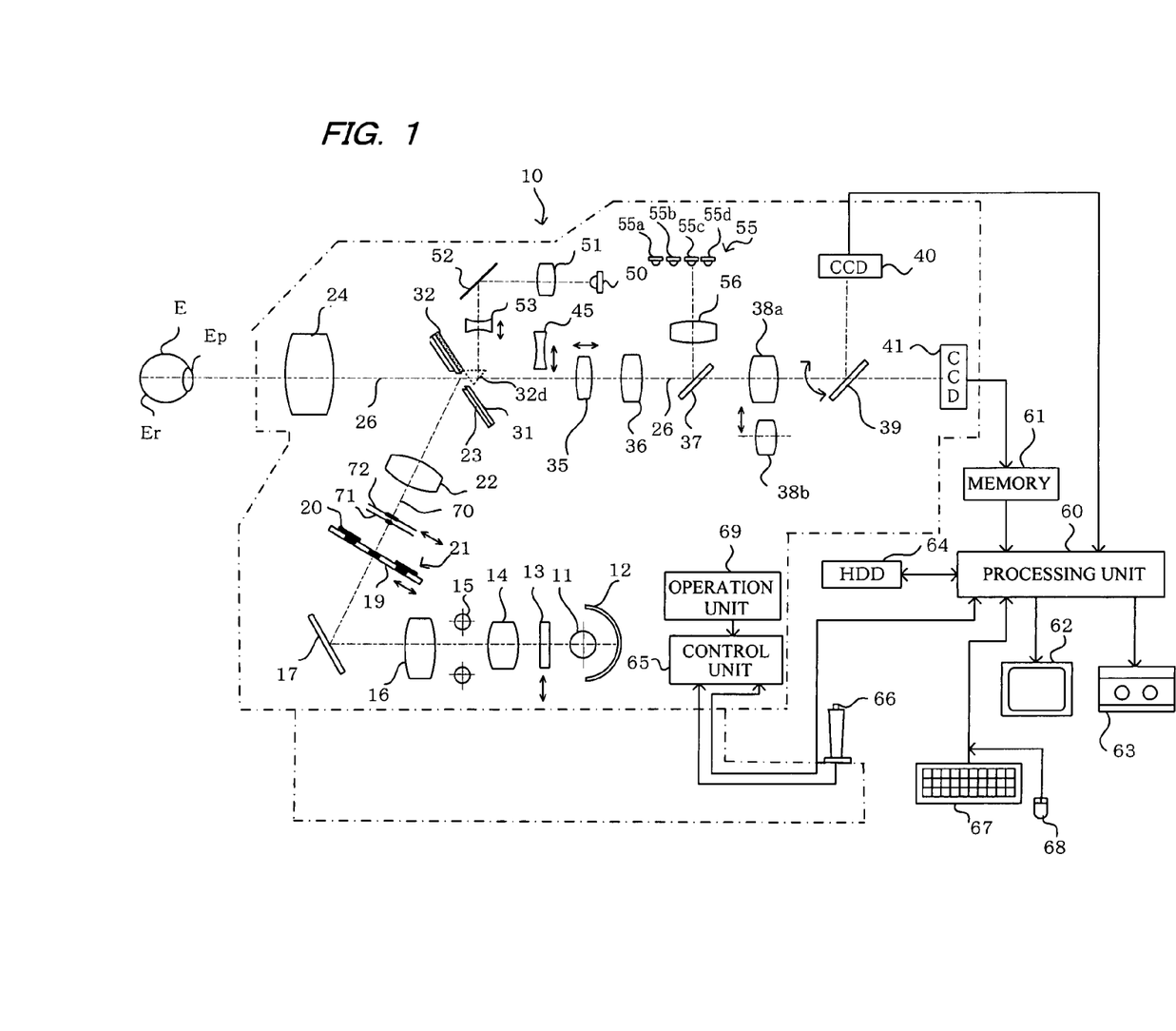
FIG. 1 is a structural view showing an optical system of an ophthalmic photography apparatus of the present invention.

In FIG. 1, an ophthalmic photography apparatus of the present invention is configured as a fundus camera 10.

In the fundus camera 10, an observation lamp 11 for emitting visible and infrared light for illumination is disposed in the center of curvature of a spherical mirror 12. The light from the observation lamp 11 and the spherical mirror 12 passes through a visible light cutting infrared transmission filter 13 that is inserted into and retracted from the optical path, a condenser lens 14, a strobe 15, and a condenser lens 16; and impinges upon a total reflection mirror 17.

The illuminating light reflected by the total reflection mirror 17 passes through an illumination stop 21 disposed in a position substantially conjugate with an anterior ocular segment Ep (pupil) of an eye to be examined, and passes through a black spot plate 71 for monocular photography, a black spot plate 72 for stereographic photography, and a relay lens 22. The illuminating light is then reflected by an apertured total reflection mirror 23, passes through an objective lens 24 and impinges upon the anterior ocular segment Ep (pupil) of an eye E to be examined to thereby illuminate the ocular fundus Er.

The illumination stop 21 comprises a fixed stop 20 having an aperture in the center and a moveable light-shielding plate 19 that is movable relative to the fixed stop 20 and is made of a transparent glass plate having a plurality of light-shielding spots. One of the light-shielding spots moves into the aperture of the fixed stop 20 in accordance with the movement of the moveable light-shielding plate 19 to thereby provide an illumination light pattern suitable for use in monocular photography and stereographic photography.

The light reflected from the fundus Er, which has been illuminated by the light having passed through the illumination stop 21, passes through the objective lens 24, the apertured total reflection mirror 23, a fixed stop 31, a moveable stop unit 32, a focusing lens 35, an imaging lens 36, a half mirror 37, and a variable power lens 38a; and impinges upon a return mirror 39. When the return mirror 39 is positioned as shown in the drawing, the light reflected from the ocular fundus impinges upon a CCD (imaging means) 40 disposed in a position substantially conjugate with the ocular fundus and having sensitivity to infrared light to capture an image of the ocular fundus. When the return mirror 39 is withdrawn from the optical path, the light reflected from the ocular fundus impinges upon a CCD (imaging means) 41 disposed in a position substantially conjugate with the ocular fundus and having sensitivity to visible light to capture an image thereof.

Figure 2A:
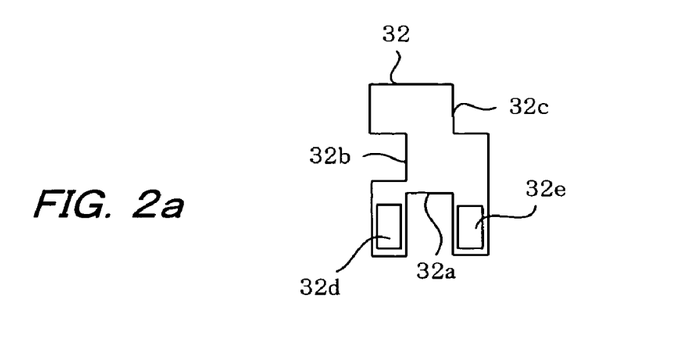
FIG. 2a is a plan view showing a structure of a moveable stop unit.
Figure 2B:
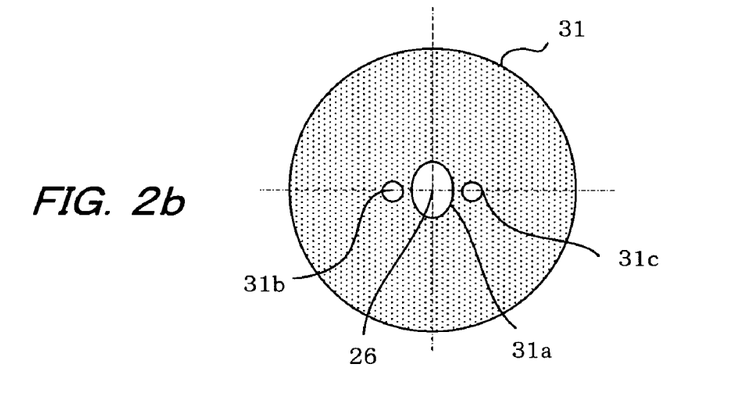
FIG. 2b is a plan view showing a structure of a fixed stop.
Figure 2C:
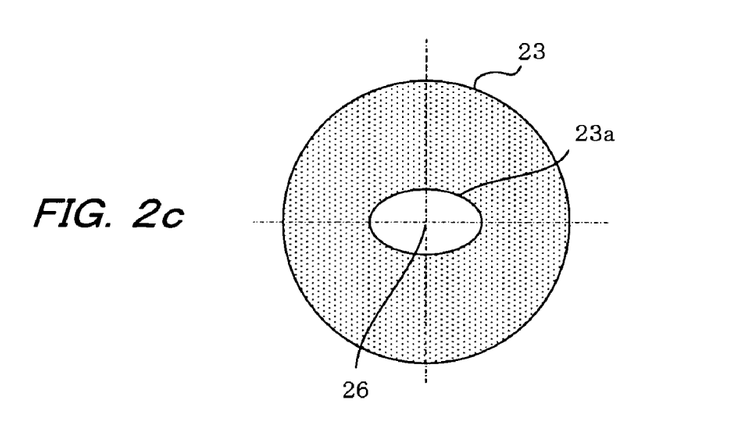
FIG. 2c is a plan view showing a structure of an apertured total reflection mirror.

As shown in FIG. 2c, the apertured total reflection mirror 23 is a circular total reflection mirror having an aperture 23a at the center. As shown in FIG. 2b, the fixed stop 31 is an stop having a photographic stop 31a for monocular photography at the center, and two photographic stops 31b, 31c on both sides thereof that are used to project a focus marker and used as a photographic stop for stereographic photography. The fixed stop 31 is affixed to the apertured total reflection mirror 23 with the center of the fixed stop 31 in alignment with the center of the apertured total reflection mirror 23.

The photographic stops 31a, 31b, 31c are disposed in a position substantially conjugate with the anterior ocular segment (pupil) of an eye to be examined. The photographic stop 31a is disposed in a position in which the center thereof is aligned with an observing and photographing optical axis 26. The photographic optical path 26 is split to the left and right in the position conjugate with the pupil in order to capture stereographically viewed left and right images. The photographic stop 31b is disposed in a position on the left side of the split optical path while the photographic stop 31c is disposed in a position on the right side thereof.

The moveable stop unit 32 is configured as shown in FIG. 2a. In the case of monocular photography, the moveable stop unit 32 moves to the position shown in FIG. 3a where a notch 32a thereof opens the aperture of the photographic stop 31a and make the photographic stop 31a effective. In a case where the stereographically viewed left and right images are to be obtained in stereographic photography, the moveable stop unit 32 moves to the positions shown in FIGS. 3b and 3c where notches 32b, 32c thereof opens the apertures of the photographic stops 31b, 31c and make the photographic stops 31b, 31c effective, respectively.

As described below, a focus correction lens 45 is disposed in the observation and photographic optical path so as to be capable of being inserted into the optical path and removed therefrom. The focus correction lens 45 corrects the defocus caused by the photographic stop 31b, 31c being decentered with respect to the photographic optical axis.

Figure 7A:
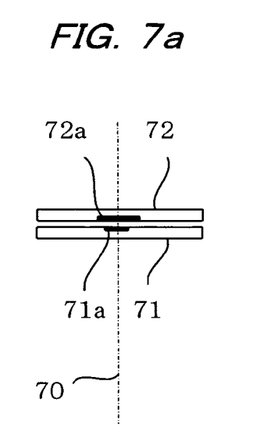
FIG. 7a is an illustrative view showing black spots in stereographic photography.
Figure 7B:
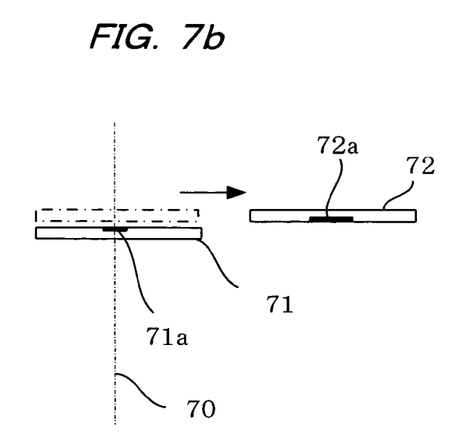
FIG. 7b is an illustrative view showing black spots in monocular photography.
Figure 8A:
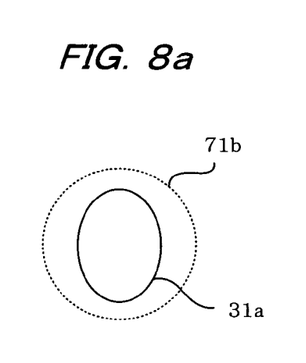
FIG. 8a is an illustrative view showing a black spot image formed at the photographic stop in monocular photography.
Figure 8B:
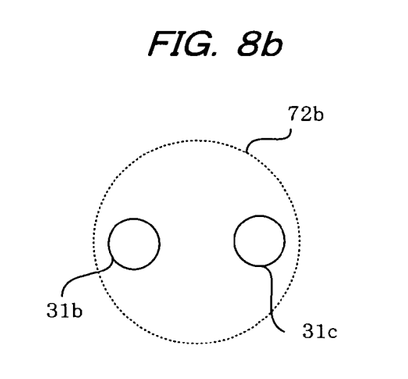
FIG. 8b is an illustrative view showing a black spot image formed at the photographic stop in stereographic photography.

The black spot plate 71 for monocular photography that is disposed in the illuminating optical system has a circular black spot 71a at the center, as shown in FIG. 7a. The black spot plate 72 for stereographic photography has a circular black spot 72a at the center. The black spots 71a, 72a are located at positions substantially conjugate with the photographic stop 31a, 31b, 31c with respect to the imaging by the photographic light reflected from the objective lens 24. As described below, when a stereographic photography mode is selected, the black spot plates 71, 72 are positioned with the centers of the black spots 71a, 72a aligned with an optical axis 70 of the illuminating optical system, as shown in FIG. 7a. Conversely, when a monocular photography mode is selected, the black spot plate 72 is removed from the optical axis 70 of the illuminating optical system to make the black spot plate 71 effective, as shown in FIG. 7b. The size of the black spot 71a for monocular photography is set so that an image 71b of the black spot 71a on the photographic stop surface will cover the entirety of the photographic stop 31a, as shown in FIG. 8a. The black spot 72a for stereographic photography is formed large enough so that, when stereographically viewed images are captured, an image 72b of the black spot 72a on the photographic stop surface will cover the entirety of the photographic stops 31b, 31c, as shown in FIG. 8b.

An optical system for projecting a focus marker is provided to the fundus camera 10. Light from a focus marker light source 50 made of an infrared LED passes through a lens 51, a mirror 52, and a lens 53. The optical path is divided in two by reflection prisms 32d, 32e, which are secured to the moveable stop unit 32 to project the focus marker onto the fundus Er. When the fundus is in focus, the focus marker images reflected by the reflection prisms 32d, 32e merge into one; when the fundus is not in focus, the images remain separate. Therefore, the examiner can bring the fundus into focus by moving the lens 53 and aligning the focus marker images in accordance with the movement of the focusing lens 35.

An internal fixation lamp 55 comprising a plurality of fixation lamps 55a to 55d is provided in order to cause the eye to be examined to fixate on the fundus camera. Light from the switched-on fixation lamp is reflected by the half mirror 37 before passing through the objective lens 24, and is projected onto the fundus Er. Therefore, the patient can fixate on the internal fixation lamp to keep the eye to be examined in a prescribed position with respect to the fundus camera.

A control unit 65 comprising a CPU or the like is provided to the fundus camera 10. The control unit 65, which is connected to a processing unit 60, exchanges signals therewith, causes the return mirror 39 to withdraw from the optical path when a shutter switch 66 is operated, and causes the strobe 15 to emit a suitable amount of light. The control unit 65 further performs a control so that the focus correction lens 45, the black spot plate 72 for stereographic photography, the visible light cutting infrared transmission filter 13, and the variable power lenses 38a, 38b are inserted into and retracted from the optical path. The control unit 65 also controls the movement of the moveable stop unit 32 and the moveable light-shielding plate 19.

An operation unit (operation panel) 69 having a photography mode selection switch is provided to the fundus camera 10 to select monocular photography, stereographic photography, and other modes of photography. A keyboard 67, a mouse 68, and other input means are also provided to the fundus camera 10 to allow a variety of data to be input.

In such a fundus camera, the imaging mode select switch on the operation unit 69 is operated for monocular photography and stereographic photography.

Figure 3A:
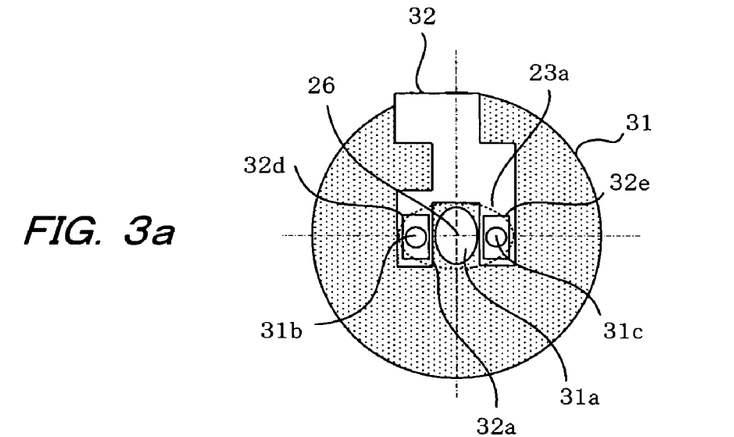
FIG. 3a is a plan view showing a state wherein a photographic stop for monocular photography is selected.

In the case of monocular photography, the moveable stop unit 32 is moved to the position shown in FIG. 3a to make the photographic stop 31a effective, and the moveable light shielding plate 19 is moved in conjunction therewith to form an illumination light pattern suitable for monocular photography. The light from the fundus, which is illuminated using infrared light, passes through an aperture 23a of the apertured total reflection mirror 23 and the photographic stop 31a, and forms an image on the CCD 40. The image can be displayed on a monitor 62, so that the examiner can observe the image of the fundus for alignment and turn on the focus marker light source 50 to bring the fundus into focus.

When the alignment and focus adjustments are complete, the shutter switch 66 is operated to cause the return mirror 39 to be retracted from the optical path and the strobe 15 to emit light. An image of the fundus illuminated by the light emitted from the strobe 15 is formed on the CCD 41. The image is recorded in a memory 61 in association with the position of the photographic stop concerned and other photographic conditions.

Figure 3B:
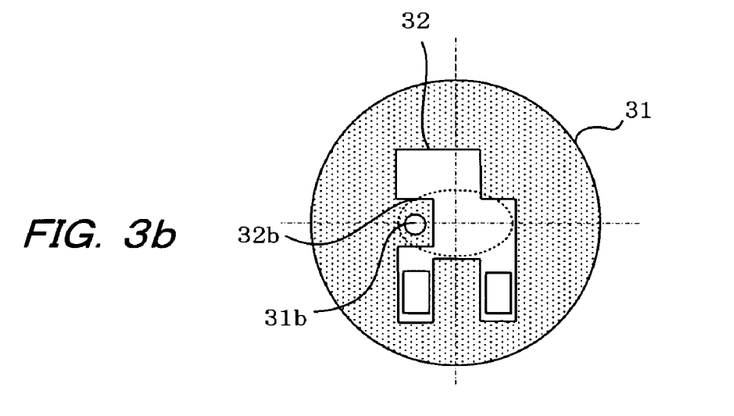
FIGS. 3b and 3c are a plan view showing a state wherein a photographic stop for stereographic photography is selected.

In the case of stereographic photography, the moveable stop unit 32 is moved to the position shown in FIG. 3b to make the photographic stop 31b effective, and the moveable light shielding plate 19 is moved so that an illumination light pattern suitable for stereographic photography is obtained. When the shutter switch 66 is operated, the strobe 15 emits light, and a stereographically viewed left image of the fundus is captured by the CCD 41 via the photographic stop 31b. Next, the moveable stop unit 32 moves to the position shown in FIG. 3c to make the photographic stop 31c effective, the strobe 15 emits light, and a stereographically viewed right image of the fundus is captured by the CCD 41 via the photographic stop 31c. In the case of stereographic photography, the photographic stops 31b and 31c are thus switched over automatically and two left and right fundus images are successively captured by a single shutter operation. The two left and right images are recorded in the memory 61 in association with the position of the photographic stops when the images were captured and other photographic conditions.

The images obtained by monocular photography and stereographic photography and recorded in the memory 61, as described above, are transmitted to an external recording device 64 at a prescribed time.

When the monocular image recorded in the memory 61 or the external recording device 64 is retrieved and displayed, a regular monitor 62 is automatically selected. When the two left and right images obtained by stereographic photography are retrieved and the fundus is stereographically viewed, a stereo monitor 63 is used, and the left and right fundus images are respectively arranged and displayed on the left and right sides of the monitor.

Figure 3C:
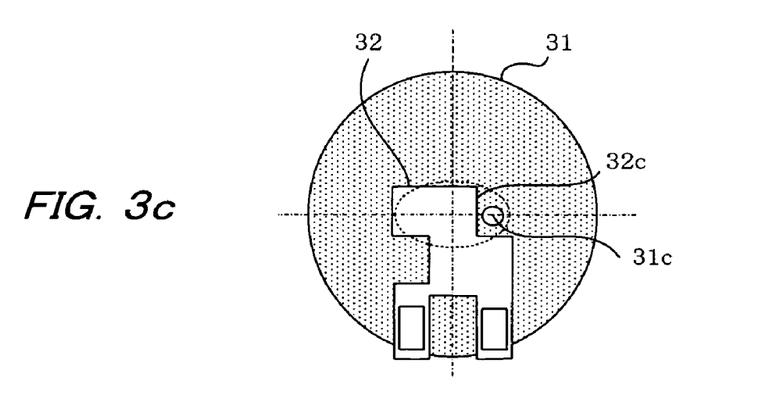
Figure 4:
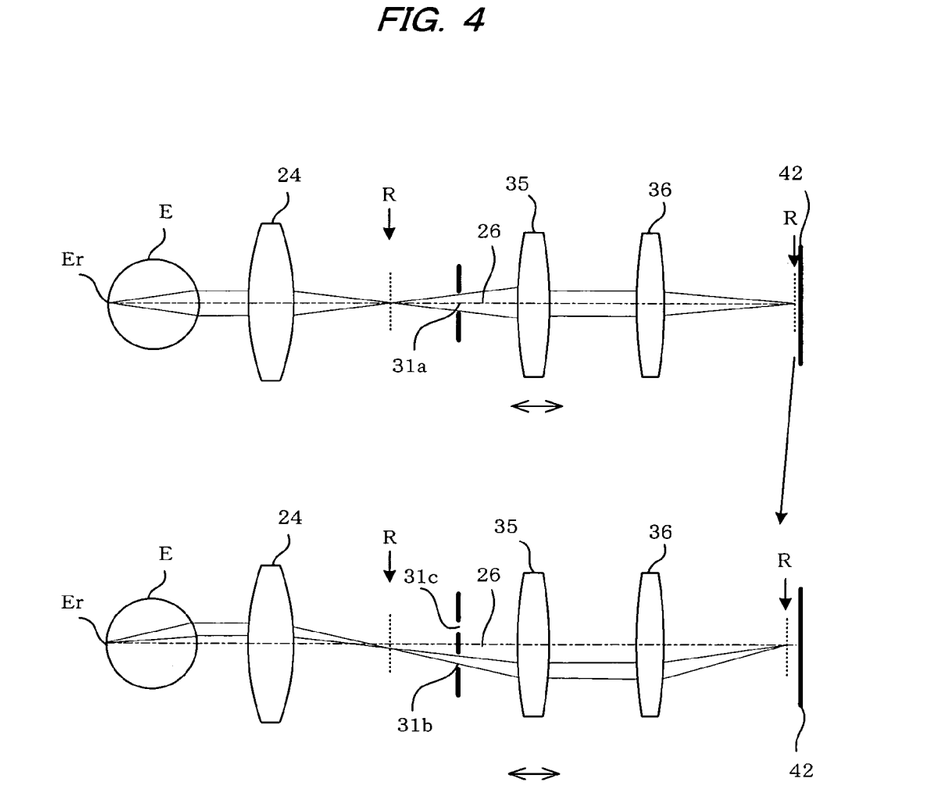
FIG. 4 is an illustrative view showing that stereographically viewed images are in defocus.
Figure 5:
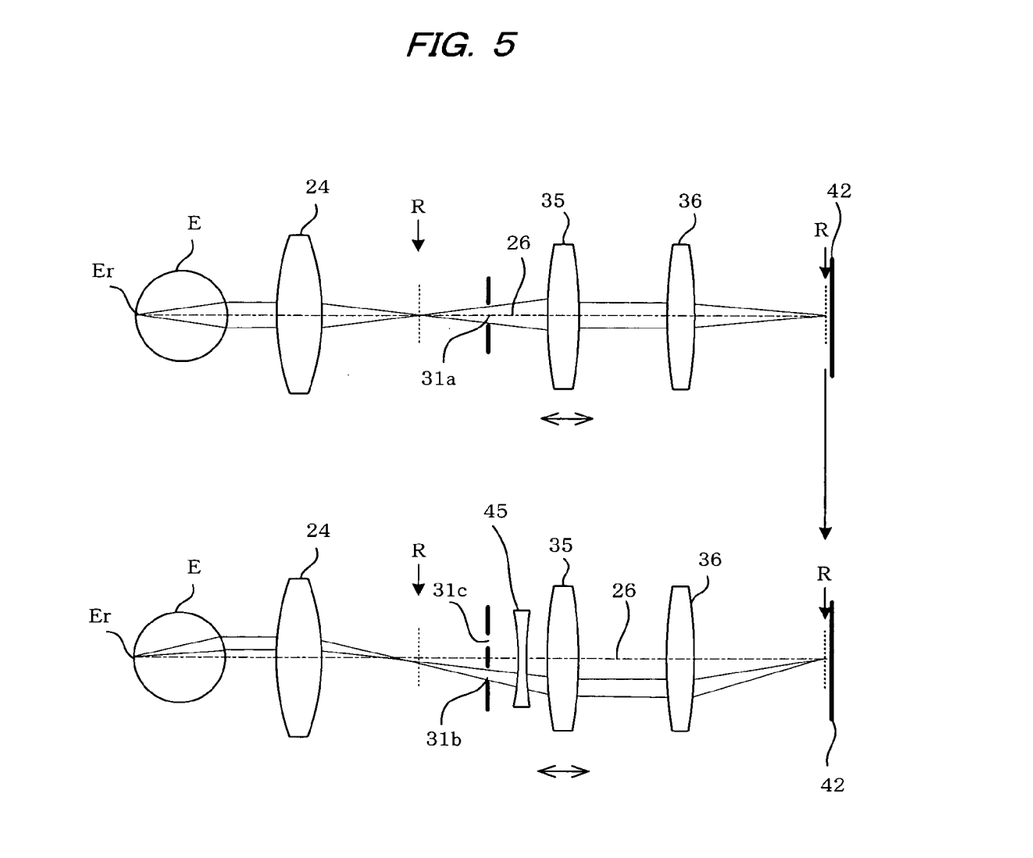
FIG. 5 is an illustrative view showing that a corrective lens is used to correct focus in stereographic photography.

FIGS. 4 and 5 are diagrams showing the principal parts of the observation and photographic optical system of the fundus camera described above. The representative optical elements illustrated in FIGS. 1 to 3 are shown using the same symbols. The symbol R in FIGS. 4 and 5 indicates a position conjugate with the fundus Er of the eye E to be examined.

The upper portions of FIGS. 4 and 5 are diagrams showing when the photographic stop 31a is selected for monocular photography, wherein the center of the photographic stop 31a is aligned with the photographic optical axis 26. The focusing lens 35 is caused to move for focus adjustment in order to produce a clear image of the fundus on a reticle observation surface 42 that is disposed in a position conjugate with the imaging surfaces of the CCD 40 and the CCD 41. Should the shutter switch 66 be operated in this state, a focused clear fundus image will be captured by the CCD 41.

However, when the photographic stop 31b or 31c is selected for stereographic photography in this state, the photographic stop 31b or 31c is decentered with respect to the photographic optical axis 26, as shown in the lower portion of FIG. 4. Consequently, the focal plane R that occupies a conjugate position with the fundus is caused to deviate from the reticle surface 42, and also deviate from the imaging surface of the CCD 41, so that an image of the fundus cannot be captured clearly.

Figure 6A:
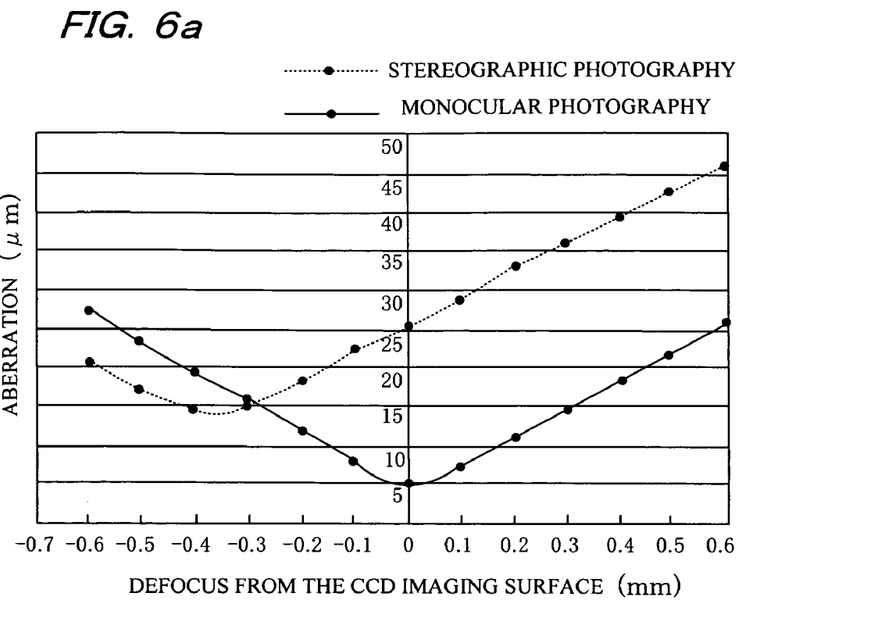
FIG. 6a is a graph showing the relationship between the amount of defocus and the amount of aberration in monocular photography and stereographic photography when no focus correction is made.

FIG. 6a shows the degradation of images due to defocus. In monocular photography, the amount of aberration is minimized (solid line) when the amount of defocus relative to the imaging surface of the CCD 41 is zero. However, the amount of defocus at which the amount of aberration is minimized is not zero in stereographic photography, but approximately −0.4 mm (dotted line), and the images obtained by stereographic photography are out of focus and unclear.

Accordingly, the focus correction lens 45 is inserted into the observation and photographic optical path between the photographic stops 31b, 31c and the focusing lens 35, as shown in the lower portion of FIG. 5. The focus correction lens 45 is inserted via a control performed by the control unit 65 when stereographic photography is selected by the operation unit 69. The focal plane R that occupies a conjugate position with the fundus moves to the reticle surface 42 as a result of insertion of the focus correction lens 45. Consequently, a focused fundus image can be observed through the CCD 40, and a focused, clear fundus image can be captured by the CCD 41. This thus allows favorable monocular fundus images and stereographically viewed fundus images to be obtained.

Figure 6B:
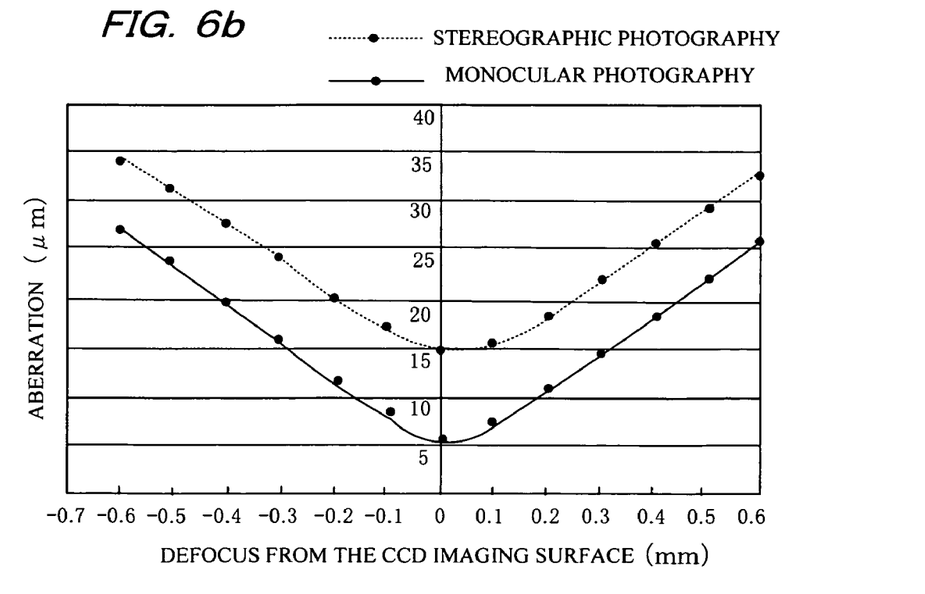
FIG. 6b is a graph showing the relationship between the amount of defocus and the amount of aberration in monocular photography and stereographic photography when focus correction is made.

FIG. 6*b* shows the effect obtained when the focus correction lens 45 is used. For both monocular photography and stereographic photography modes, the amount of aberration is minimized when the amount of defocus is zero, thus allowing favorable monocular fundus images and stereographically viewed fundus images to be obtained.

In the above-mentioned embodiment, an optical lens is used as an optical element for correcting defocus due to the photographic stops for stereographic photography being decentered from the photographic optical axis. However, it is also possible to use an optical element such as an optical length correcting glass plate that corrects an optical length corresponding to the difference between the length of an optical path when a monocular image is to be captured and the length of an optical path when stereographically viewed images are to be captured.

An optical lens or optical length correction glass is inserted into the photographic optical path as a corrective optical element when stereographically viewed images are to be captured. It is also possible to adopt an arrangement in which the focus is set when stereographically viewed images are to be captured, and the corrective optical element is inserted into the photographic optical path to correct the defocus caused when the photography mode is switched from the stereographic to monocular photography. In this case, the optical lens is a convex lens, which is the opposite of that used when stereographically viewed images are captured.

The corrective optical element is inserted between the photographic stop and the focusing lens, but may also be inserted into the optical path on the side of the photographic stop opposite the eye to be examined; i.e., the optical path between the photographic stop and the imaging means (CCD 40, 41).

In the embodiment described above, a corrective optical element is used to correct defocus during observation and/or when an image is captured. However, defocus may also be corrected by causing the optical element for bringing the fundus into focus; i.e., the focusing lens 35, or the CCD 40, 41, to move along the observation and photographing optical axis. In this case, if the fundus is brought into focus in monocular photography to observe the eye and capture its image, then the focusing lens 35 or the CCD 40, 41 is caused to move along the optical axis in stereographic photography by a length corresponding to a difference between the lengths of the optical path in the monocular and stereographic photography modes so as to be able of clearly observing and capturing stereographically viewed images. Conversely, if the fundus is brought into focus in stereographic photography to capture stereographically viewed images, then the focusing lens 35 or the CCD 40, 41 is caused to move along the observation and photographing optical axis in monocular photography by a length corresponding to a difference between the lengths of the optical path in the monocular and stereographic photography modes so as to be able of observing and capturing a focused monocular image. Moving the focusing lens 35 or the CCD 40, 41 by a length corresponding to the difference in the optical lengths can be performed manually by using a button provided to the operation unit 69, or automatically via a control performed by the control unit 65.

When a monocular image is captured, the black spot plate 72 for stereographic photography is removed from the optical axis 70 of the illuminating optical system in order to make effective the black spot plate 71 for monocular photography, as shown in FIG. 7*b*. The image 71*b* of the black spot 71*a* on the surface of the photographic stop 31*a* covers the entirety thereof, as shown in FIG. 8*a*. This allows the photographic light reflected by the objective lens 24 to be prevented from passing through the photographic stop 31*a* and the quality of the captured fundus image to be improved.

However, if the photographic stops 31*b*, 31*c* are used in stereographic photography without black spot adjustment, it will be impossible to adequately prevent photographic light from being reflected by the objective lens, and artifacts in the form of a white spot will appear in the center of the captured fundus images, thus deteriorating the quality and reliability of the stereographically viewed images.

Accordingly, when stereographic photography is performed, the black spot plate 72 for stereographic photography is inserted into the illuminating optical path 70 by the control unit 65, as shown in FIG. 7*a*. For each case where an image is captured via either the photographic stop 31*b* or the photographic stop 31*c*, the image 72*b* of the black spot 72*a* on the photographic stop surface will cover the entirety of the photographic stops 31*b*, 31*c*, as shown in FIG. 8*b*. This allows the photographic light reflected by the objective lens surface to be prevented from passing through the photographic stops 31*b*, 31*c* and the quality of the stereographically viewed fundus images to be improved.

Figure 9A:
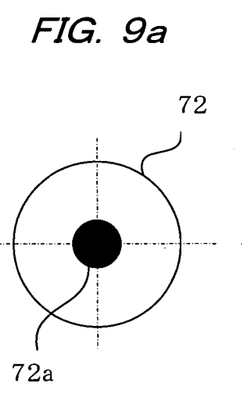
FIG. 9a is a plan view showing an embodiment of an black spot plate.
Figure 9B:
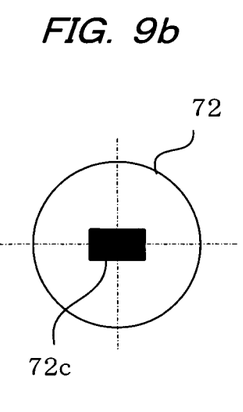
FIG. 9b is a plan view showing another embodiment of an black spot plate.
Figure 9C:
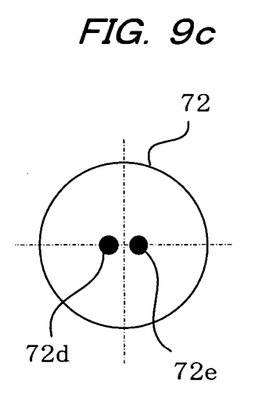
FIG. 9c is a plan view showing still another embodiment of an black spot plate.

The shape and quantity of the black spots formed on the black spot plate 72 for stereographic photography can be changed. For example, FIG. 9*a* shows an example where a circular black spot 72*a* is formed on the black spot plate 72, as is the case with the black spot plate in FIG. 7. The circular black spot 72*a* can be altered to become a rectangular black spot 72*c*, as shown in FIG. 9*b*, or two separate circular black spots 72*d*, 72*e* can be formed on the black spot plate 72, as shown in FIG. 9*c*. It will be apparent that in whichever example the size of the black spot is such that, when the black spot plate 72 is inserted into the optical path in the stereographic photography, the image of the black spots 72*a*, 72*c*, 72*d*, 72*e* on the photographic stop surface will cover the photographic stops 31*b*, 31*c* so as to prevent the photographic light reflected by the objective lens surface from passing through the photographic stops 31*b*, 31*c*.

Figure 10:
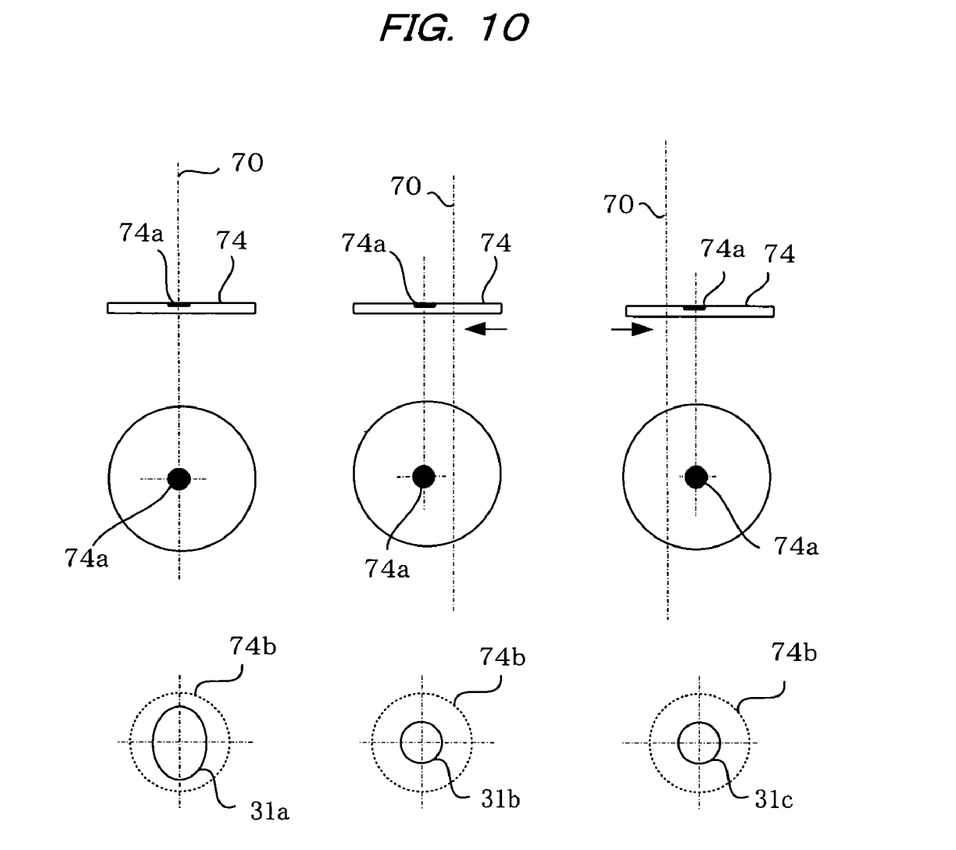
FIG. 10 is an illustrative view showing a state in which the black spots are changed according to the photography mode.

As shown in FIG. 10, a single black spot plate 74 in whose center is formed a circular black spot 74*a* may also be employed. The black spot plate 74 is caused to move left or right in a direction that is perpendicular to the optical axis 70 of the illuminating optical system under the control performed by the control unit 65.

In the state shown on the left of FIG. 10, the center of the black spot 74*a* is aligned with the optical axis 70 and the photographic stop 31*a* is selected for monocular photography. The image 74*b* of the black spot 74*a* at the photographic stop 31*a* entirely covers the photographic stop 31*a*, as shown on the lower left of the drawing. In the state shown in the center of FIG. 10, the black spot plate 74 moves leftward from the optical axis 70 when the photographic stop 31*b* is selected for stereographic photography. The image 74*b* of the black spot 74*a* at the photographic stop 31*b* entirely covers the photographic stop 31*b*, as shown in the lower center of the drawing. In the state shown on the right of FIG. 10, the black spot plate 74 moves rightward from the optical axis 70 when the photographic stop 31*c* is selected for stereographic photography. The image 74*b* of the black spot 74*a* at the photographic stop 31*c* entirely covers the photographic stop 31*c*, as shown on the lower right of the drawing. In all cases, the photographic light reflected by the objective lens surface is prevented from passing through the photographic stops 31*a*, 31b, 31c and from reflecting at the objective lens, thus improving the quality of the fundus image. It will be apparent that a variety of configurations may be adopted for switching and selecting the black spots, as described in Japanese Laid-open Patent Publication No. 2007-185324; and that the shape of the black spot 74a need not be circular, but can be rectangular or of another shape.

What is claimed is:

1. An ophthalmic photography apparatus comprising:
   an imaging device that captures a monocular image of a fundus of an eye under examination via a photographic stop for monocular photography during operation in a monocular photographic mode and that captures stereographically viewed images of the fundus with a parallax via photographic stops that are decentered relative to a photographic optical axis for stereographic photography during operation in a stereographic photography mode;
   an operation unit that switches between operation in the monocular photographic mode and operation in the stereographic photography mode;
   an illuminating optical system that illuminates the fundus of the eye under examination via an objective lens;
   a photographic optical system that guides light from the fundus of the eye under examination through the objective lens to the imaging device via the photographic stop during operation in the monocular photographic mode and via the photographic stops during operation in the stereographic photography mode;
   a first black spot plate disposed in the illuminating optical system and having at least one first black spot that prevents photographic light reflected from the objective lens from passing through the photographic stop during operation in the monocular photography mode; and
   a second black spot plate disposed in the illuminating system and having at least one second black spot that prevents photographic light reflected from the objective lens from passing through the two photographic stops during operation in the stereographic photography mode.

2. An ophthalmic photography apparatus according to claim 1; wherein the first and second black spot plates are mounted for undergoing movement in at least one of a direction along an optical axis of the illuminating optical system and a direction perpendicular to the optical axis so that the corresponding at least one of the first and second black spots move in the at least one of the direction along the optical axis and the direction perpendicular to the optical axis during operation in the corresponding monocular and stereographic photography modes.

3. An ophthalmic photography apparatus according to claim 1; wherein each of the at least one of the first black spot and the at least one of the second black spot comprises a plurality of black spots, at least two black spots of the corresponding at least one of the first black spot and at least one of the second black spots being disposed so as to be superimposed as viewed from the optical axis of the illuminating optical system depending upon positions of the photographic stops during operation in the corresponding monocular and stereographic photography modes.

4. An ophthalmic photography according to claim 1; further comprising a corrective optical element that is selectively inserted into or retracted from the photographic optical axis to correct defocus resulting from stops for stereographic photography that are decentered relative to the photographic optical axis switching between operation in the monocular mode and operation in the stereographic mode.

5. An ophthalmic photography apparatus according to claim 4; wherein the corrective optical element comprises an optical lens.

6. An ophthalmic photography apparatus according to claim 5; wherein the corrective optical element comprises an optical element that corrects an optical length of an optical path during operation in the monocular photography and a length of an optical path during operation in the stereographic photography mode.

7. An ophthalmic photography apparatus according to claim 5; further comprising a control unit that selectively inserts the corrective optical element into the photographic optical axis and retracts the corrective optical element from the photographic optical axis; wherein the control unit inserts the corrective optical element into the photographic optical axis between the two photographic stops and the imaging means during operation in the stereographic photography mode, and retracts the corrective optical element from the photographic optical axis during operation in the monocular photography mode.

8. An ophthalmic photography apparatus according to claim 5; further comprising a control unit that selectively inserts the corrective optical element into the photographic optical axis and retracts the corrective optical element from the photographic optical axis; wherein the control unit inserts the corrective optical element into the photographic optical axis in the monocular photography mode into a photographic optical path between the photographic stop and the imaging device during operation in the monocular photography mode, and retracts the corrective optical element from the photographic optical axis during operation in the stereographic photography mode.

9. An ophthalmic photography apparatus according to claim 4; wherein the corrective optical element is mounted to undergo movement along the photographic optical axis to correct defocus resulting from switching between operation in the monocular mode and operation in the stereographic mode by moving along the photographic optical axis by a length corresponding to a difference between a length of an optical path during operation in the monocular photography mode and a length of an optical path during operation in the stereographic photography mode.

10. An ophthalmic photography apparatus according to claim 4; wherein the corrective optical element corrects defocus resulting from switching the operation in the monocular photographic mode to operation in the stereographic mode due to the two photographic stops for stereographic photography being decentered relative to the photographic optical axis.

* * * * *